(12) United States Patent
Amiot et al.

(10) Patent No.: US 11,723,585 B2
(45) Date of Patent: Aug. 15, 2023

(54) IMPLANTS, SYSTEMS AND METHODS FOR SURGICAL PLANNING AND ASSESSMENT

(71) Applicant: Biomet Manufacturing, LLC, Warsaw, IN (US)

(72) Inventors: Louis-Philippe Amiot, Montreal (CA); Joseph Michael O'Reilly, Granger, IN (US); Kenyon Mumford, Warsaw, IN (US); Alfredo Castaneda, Miami, FL (US); Robert M. Ronk, Warsaw, IN (US); Marcus Bourda, Miami, FL (US); Robert Sixto, Miami, FL (US); Brian M. May, Orange, CT (US); Stephen J. Vankoski, Fort Wayne, IN (US); Orsa Britton, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 746 days.

(21) Appl. No.: 16/737,448

(22) Filed: Jan. 8, 2020

(65) Prior Publication Data
US 2020/0138361 A1    May 7, 2020

Related U.S. Application Data

(63) Continuation of application No. 15/624,184, filed on Jun. 15, 2017, now Pat. No. 10,561,360.
(Continued)

(51) Int. Cl.
*A61B 5/00* (2006.01)
*A61B 5/11* (2006.01)
(Continued)

(52) U.S. Cl.
CPC .......... *A61B 5/4504* (2013.01); *A61B 5/0022* (2013.01); *A61B 5/0031* (2013.01);
(Continued)

(58) Field of Classification Search
CPC .......... A61B 5/0022; A61B 2562/0261; A61B 5/4848; A61B 2560/0271;
(Continued)

(56) References Cited

U.S. PATENT DOCUMENTS

| | | |
|---|---|---|
| 7,691,130 B2 | 4/2010 | Bruneau et al. |
| 8,016,859 B2 | 9/2011 | Donofrio et al. |

(Continued)

FOREIGN PATENT DOCUMENTS

| | | |
|---|---|---|
| WO | WO-2016076838 A1 | 5/2016 |

OTHER PUBLICATIONS

U.S. Appl. No. 15/624,184, filed Jun. 15, 2017, Implants, Systems and Methods for Surgical Planning and Assessment.
(Continued)

*Primary Examiner* — Christine H Matthews
*Assistant Examiner* — Joshua Daryl D Lannu
(74) *Attorney, Agent, or Firm* — Schwegman Lundberg & Woessner, P.A.

(57) ABSTRACT

Example implants, systems and methods using sensors for orthopedic surgical assessment and/or planning are described herein. An example system can include a wearable sensor device for pre-operative use by a patient before an orthopedic surgery to generate pre-operative sensor data. The system can also include an implantable sensor device (e.g., a bone implant) to generate and aggregate post-operative sensor data associated with the patient after the surgery. The system can retrieve the pre-operative sensor data and the post-operative sensor data and predict, analyze or assess an outcome of the surgery.

20 Claims, 11 Drawing Sheets

Related U.S. Application Data

(60) Provisional application No. 62/398,655, filed on Sep. 23, 2016, provisional application No. 62/350,314, filed on Jun. 15, 2016.

(51) Int. Cl.
*A61B 5/07* (2006.01)
*G16H 40/67* (2018.01)
*G16Z 99/00* (2019.01)

(52) U.S. Cl.
CPC ............ *A61B 5/076* (2013.01); *A61B 5/1118* (2013.01); *A61B 5/4848* (2013.01); *A61B 5/686* (2013.01); *A61B 5/746* (2013.01); *G16H 40/67* (2018.01); *G16Z 99/00* (2019.02); *A61B 2505/05* (2013.01); *A61B 2560/028* (2013.01); *A61B 2560/0271* (2013.01); *A61B 2560/0276* (2013.01); *A61B 2562/0219* (2013.01); *A61B 2562/0261* (2013.01); *A61B 2562/0271* (2013.01)

(58) Field of Classification Search
CPC ...... A61B 2560/0276; A61B 2560/028; A61B 2562/0219; A61B 2562/0271; A61B 5/4504; A61B 5/076; A61B 5/1118; A61B 5/686; A61B 5/746; A61B 2505/05; A61B 5/0031; G06F 19/00; G16H 40/67
See application file for complete search history.

(56) References Cited

U.S. PATENT DOCUMENTS

| | | | |
|---|---|---|---|
| 8,029,566 B2 | 10/2011 | Lozier et al. | |
| 8,956,418 B2 | 2/2015 | Wasielewski et al. | |
| 9,299,138 B2 | 3/2016 | Zellner et al. | |
| 9,375,222 B2 | 6/2016 | Fitz et al. | |
| 2004/0171924 A1 | 9/2004 | Mire et al. | |
| 2007/0232958 A1 | 10/2007 | Donofrio et al. | |
| 2007/0238992 A1* | 10/2007 | Donofrio | A61B 8/56 600/437 |
| 2008/0033442 A1 | 2/2008 | Amiot et al. | |
| 2008/0269596 A1 | 10/2008 | Revie et al. | |
| 2010/0100011 A1* | 4/2010 | Roche | A61B 5/103 623/20.14 |
| 2011/0213221 A1 | 9/2011 | Roche | |
| 2014/0275815 A1* | 9/2014 | Stein | A61B 5/4528 600/300 |
| 2014/0277542 A1* | 9/2014 | Stein | A61F 2/4657 623/20.32 |
| 2015/0012631 A1* | 1/2015 | Udani | H04W 4/029 709/223 |
| 2015/0100245 A1* | 4/2015 | Huang | A61B 5/1118 600/509 |
| 2015/0238150 A1* | 8/2015 | Subramaniam | G08B 21/0446 340/539.11 |
| 2016/0128573 A1 | 5/2016 | Wilder et al. | |
| 2016/0157940 A1 | 6/2016 | Stein et al. | |
| 2017/0360358 A1 | 12/2017 | Amiot et al. | |

OTHER PUBLICATIONS

"U.S. Appl. No. 15/624,184, Non Final Office Action dated May 10, 2019", 15 pgs.

"U.S. Appl. No. 15/624,184, Notice of Allowance dated Oct. 8, 2019", 11 pgs.

"Application Serial No. 15/624,184, Response filed Aug. 7, 2019 to Non Final Office Action dated May 10, 2019", 13 pgs.

"The Right Stuff for Super Spaceships", Science@NASA, [Online]. Retrieved from the Internet: <http:science.nasa.gov/headlines/y2002/16sep_rightstuff.htm7/2/2008>, (Sep. 16, 2012), 7 pgs.

Bergmann, G, et al., "Frictional Heating of Total Hip Implants, Part 1 Measurement in Patients", J of Biomechanics, vol. 34, (2001), 421-428.

Bergmann, G, et al., "Hip Joint Loading During Walking and Running Measured in Two Patients", J of Biomechanics, vol. 26 Issue 8, (1993), 969-990.

Brick, J F, et al., "The Patellofemoral Component of Total Knee Arthoplasty", Clin Orthop, vol. 231, (1988), 163-178.

Cooper, James A, et al., "Fiber-Based Tissue-Engineered Scaffold for Ligament Replacement: Design Considerations and In Vitro Evaluation", Biomaterials 26; Elsevier Ltd., (2005), 1523-1532.

Davy, D T, "Telemetric Measurements Across the Hip After Total Arthoplasty", J of Bone and Joint Surgery, vol. 70-A Issue 1, (1998), 445-50.

Fehring, T K, et al., "Early Failures in Total Knee Orthoplasty", Clin Orthop, (2001), 315-318.

Kaufman, K R, et al., "Instrumented Implant for Measuring Tibiofemoral Forces", J of Biomechanics, vol. 29 Issue 5, (1996), 667-671.

Kotzar, G M, et al., "Telemeterized in Vivo Hip Joint Force Data: a Report on Two Patients After Total Hip Surgery", J of Ortho Research, vol. 9 Issue 5, (1989), 621-633.

Sharkey, P F, et al., "Why are Total Knee Arthoplasties Failing Today?", Clin Orthop, vol. 404, (2002), 7-13.

Shenfang, Yuan, "Determination of Internal Strain in 3-D Composites Using Optic Fiber Strain Sensors", Acta Mechanica Solida Sinica, vol. 17 No. 1, HUST Wuhan, China, (Mar. 2004), 52-57.

Taylor, S J, et al., "Forces and Moments Telemetered from Two Distal Femoral Replacement During Various Activities", J of Biomech, vol. 34, (2001), 829-848.

Wang, Zhong Lin, et al., "Piezoelectric Nanogenerators Based on Zinc Oxide Nanowire Arrays", Science, vol. 312, (Apr. 14, 2006), 242-246.

* cited by examiner

IMPLANTS, SYSTEMS AND METHODS FOR SURGICAL PLANNING AND ASSESSMENT

CLAIM OF PRIORITY

This patent application is a continuation of U.S. patent application Ser. No. 15/624,184, entitled "Implants, Systems and Methods for Surgical Planning and Assessment," filed on Jun. 15, 2017, which claims the benefit of priority of Amiot et al. U.S. Provisional Patent Application Ser. No. 62/350,314, entitled "Sensor in Bone Plate," filed on Jun. 15, 2016, each of which is hereby incorporated by reference herein in its entirety.

This patent application is also a continuation of U.S. patent application Ser. No. 15/624,184, entitled "Implants, Systems and Methods for Surgical Planning and Assessment," filed on Jun. 15, 2017, which claims the benefit of priority of Vankoski et al. U.S. Provisional Patent Application Ser. No. 62/398,655, entitled "Systems and Methods for Surgical Planning and Assessment," filed on Sep. 23, 2016, each of which is hereby incorporated by reference herein in its entirety.

TECHNICAL FIELD

This document pertains generally, but not by way of limitation, to orthopedic devices, systems and methods that employ sensors. More particularly, this document pertains to implants, systems and methods using sensing technology for surgical planning and/or assessment.

BACKGROUND

Orthopedic devices can be implanted in a patient when a body part of a patient, such as at a bone or joint, is worn, damaged, or broken, resulting in pain.

Although orthopedic devices can be implanted in a patient to resolve issues with the affected body part, sometimes, as with any other mechanical device, the implant can wear out or become damaged under excessive force. This is more common in patients who have implantation performed at a young age and the patient choses to have a very active physical lifestyle. At the other end of the spectrum, some patients are not active enough, which can also hinder recovery.

BRIEF DESCRIPTION OF THE DRAWINGS

In the drawings, which are not necessarily drawn to scale, like numerals can describe similar components in different views. Like numerals having different letter suffixes can represent different instances of similar components, sub-components of a larger logical or physical system, or the like. The drawings illustrate generally, by way of example, but not by way of limitation, various examples described in the present disclosure.

DETAILED DESCRIPTION

Figure 1:
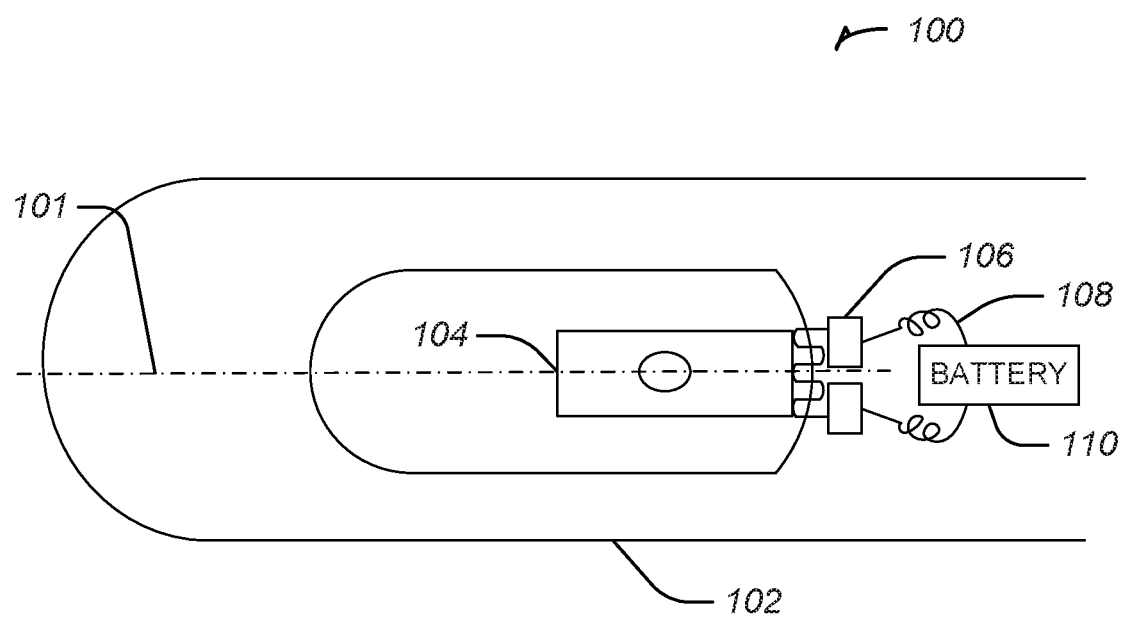
FIG. 1 illustrates a system including an implant having a sensor in accordance with at least one example.

In general, this disclosure solves challenges related to implanted orthopedic devices such as assessing how active a patient is before and after surgery, predicting or assessing the outcome of the surgery, and predicting the life of the device. These challenges can apply to a particular patient or a patient population. Other challenges that can be solved can include when a health care provider that does not have access to the original surgical plan and needs to make an independent assessment of a surgery, or make recommendations regarding post-surgical care and planning.

Systems and methods directed to sensors, sensor control and use are described herein. For example, systems and methods for sensor control, sensor technology, sensor placement in an implant, such as, but not limited to, a bone plate with integrated sensors are described herein. Systems and methods of using the sensor data to assess factors related to the surgery, the implant or the patient's response thereto, are also described herein.

A sensor can be included in an implantable orthopedic device. The implant can act as a host for the sensor or be the sensor itself. In some examples, a provider, such as a medical provider can control data related to the implant or sensor. Data can be sent to other third parties, such as the device manufacturer, surgeon, patient, etc. In another example, the patient can provide access to the data or deny access to the data to an interested party.

Instrumenting orthopedic implants, bone plates or other implanted prosthetic devices can provide useful data that can provide medical personnel with the ability to assess overall patient health, implant health, and health of the affected anatomic structure, among other things. In some examples, sensors can collect data such as forces/loads experienced by the implant, activity level of patient, failure modes of the implant, chemical processes occurring in sensor area, and even callous formation around bone fractures. Sensors can be positioned to monitor bone plate fasteners for failures or undesirable movement. Using internal sensors can assist in monitoring patients such as during recovery to determine whether the patient is performing prescribed exercises or over exerting an injured limb.

The present disclosure is also directed to systems and methods for generating a surgical plan and for assessing results of a surgery executed according to such plan. Examples according to this disclosure can be directed to employing sensor data indicative of patient-specific or orthopedic implant-specific parameters to predict the performance of a prosthetic device implanted in the patient and to evaluate the actual performance of the implant (and, in some examples, in addition to or in lieu thereof, evaluate the success of the implant procedure) by comparing the predicted performance to actual sensor data collected postoperatively.

Example systems that can implement such methods (e.g., techniques) can include wearable and/or implanted sensor devices with or without wireless communication components and capabilities, orthopedic prosthetic implants, and a computer-implemented surgical planning and assessment system. The disclosed concepts can be applied in a variety of different types of orthopedic conditions and treatments thereof, including arthroplasty to repair or replace part or all of a damaged and/or diseased joint of a patient like, as examples, a knee or shoulder joint.

Example Implant-Sensor System

FIG. 1 illustrates a system 100 including an implant 102 having a sensor 104, in accordance with some examples. The implant 102 can be inserted in a user and can include any suitable sensor 104, such as a proximity detector, sensing coil or a strain gauge 106. The implant can also include a resistor 108, and a battery 110. The sensor 104 can include a sensing coil to detect whether the implant 102 is in an open or closed position relative to another sensing coil in another implant. The battery 110 can be used to power the sensor 104 or the implant 102. The strain gauge 106 can be a sensor used to measure strain or deformation in a static or moveable portion of the implant 102 or of a user. In other examples, different types of sensors can be used, that are provided in addition to or in place of the proximity sensor, sensing coil or strain gauge, such as the sensors described below related to FIG. 4. In various examples, the implant can include a locking mechanism for hosting the sensor 10, such as by snap fit, adhesive or various types of welding including vibration welding.

In some examples, and as shown in FIG. 1, the sensor 104 can include strain gauge 106. The sensor 104 can be used to determine variable resistance on a portion of the implant 102 (e.g., a bone plate or other orthopedic device) such as along an axis 101. In various examples employing strain gauge, deformation of a strain gauge can be monitored using different voltage potential. Other example uses of a sensor can include resistance measurement (e.g., correlated to motion of the sensor), strain gauge deformation (e.g., strain gauge attached to deformable portion of an implant). Analysis of strain gauge sensor data can be used to adjust post-operative procedures and recommendations, such as recommending faster or slower weight bearing, or indicating if the patient should be more active or less active, an alarm mechanism to indicate over-exertion, or an objective measure to confirm healing. The strain gauge can be formed of metal, but any suitable strain gauge can be used. In some examples, the strain gauge can be attached to the implant proximate a proximity detector on the implant.

In another example, information related to deformation can be determined with a Fiber Braggs Grating (FBG) or flexible micro-sensors as described in US Patent Application Publication US20080033442A1, which is incorporated herein by reference. An FBG can include a flexible film formed of a mesh of optical fibers, with Braggs gratings distributed along each optical fiber. The light captured at the exit of the optical fibers provides information on the deformation of the flexible film. A 3D model can be created by associating the positions of the Braggs gratings in the optical fibers to the deformation information captured from the captured light.

Example Sensor Placement on an Implant

Figure 2:
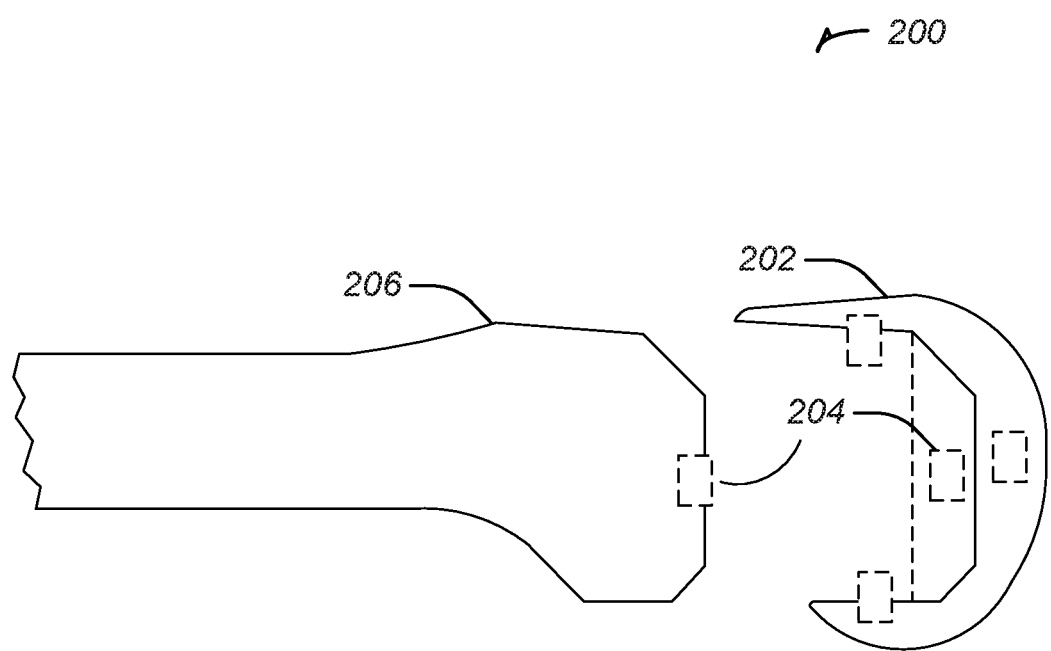
FIG. 2 illustrates example sensor placements on a bone or an implant in accordance with at least one example.

FIG. 2 illustrates example sensor (e.g., 204) placements on a bone or an implant in accordance with some examples.

The sensors (e.g., 204) can be placed at various locations on an implant 202 or on a bone 206. The placement of sensors (e.g., 204) can vary according to the type of implant 202, the properties of the bone 206, or the type of sensor. In another example, the sensor placement can be determined according to information to be collected from the sensor 204. For example, the sensor placement for sensor 204 can be used for determining and aggregating impact forces, whereas another sensor can be located to determine wear on the implant 202 or the bone 206.

Sensor placement, combinations and systems can include load or weight bearing sensors or implants. Sensors can monitor measurements on a bone plate or bone over time to determine healing, a healing indicator, or to alert the healthcare provider or patient to an issue and or suggest a corrective action, etc. A sensor can provide a measure of weight bearing on a limb externally as well as within a bone plate. A sensor or implant can monitor how much motion is the proper amount of motion to prompt healing, such as by using sensors on either side of a fracture.

In various examples, a sensor or implant can monitor callous formation. For example, a sensor or implant can include a flexible sensor stretched across a fracture that can measure deflection of the sensor due to callous formation and measure remodeling (e.g., reduction of callous to anatomical bone). In another example, motion inducing plates can promote callous formation under the plate (e.g., fixation plates far cortex measurement of callous formation), and the motion can be monitored by a sensor, such as by using callous formation sensing tape.

Undesirable movement can lead to callous formation, so a sensor that can monitor motion, load, biologic factors white/red blood cells), resistance, or the like can be provided. The movement can be highly dependent on fracture type (e.g., transverse, multiple fracture, etc.), which can be used to adjust a sensor used, an implant position, a technique for aggregating data from the sensor, or thresholds for determining issues using aggregated data.

In another example, a sensor can monitor a motion lock plate, which typically includes motion lock on one side of a fracture or on both sides. A motion-lock plate can include screw holes or screw hole inserts specifically designed to allow for micro-movement of the underlying bone to assist in promoting bone growth.

A motion lock plate can be provided in the form of a dynamic locked plate technology that uses a silicone coated threaded insert that is placed within a milled pocket with the plate. The sensors can be housed in a milled pocket on the plate and the silicone insert allowed for dynamization between the two parts, which could be measured by a change in distance or relative angle to one another.

In yet another example, a sensor can monitor motion or load data (e.g., impact force, number of impacts) to determine how much load a bone is taking over time. Information stored by an implant can include measurement modalities of a sensor, such as load, position, or motion. A sensor confirmation of plan can be sensor-specific, patient-specific, implant-specific, surgeon-specific, company-specific, manufacturer-specific, or the like.

In an example including an external fixation implementation, an implanted sensor can include a sensor that is incorporated into either an internal portion or an external portion of a fixation implant that extends into the body of the patient.

Patient Sensor Placement

Figure 3:
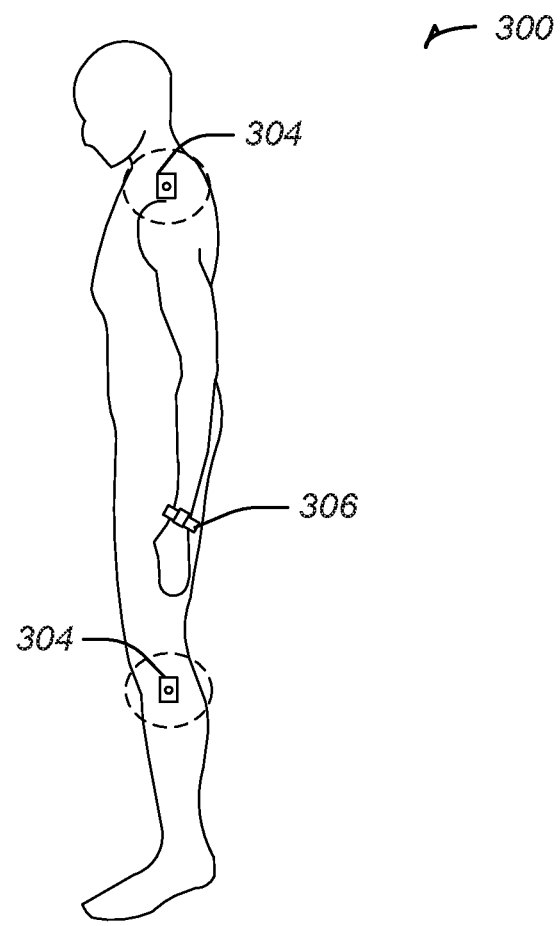
FIG. 3 illustrates sensor devices implanted within or worn by a patient in accordance with at least one example.

FIG. 3 depicts various implanted or wearable sensors that can be employed in examples according to this disclosure.

The example of FIG. 3 can include an implanted sensor 304 (e.g., a first sensor, a post-operative sensor) associated with a knee joint of the patient, an implanted sensor 304 (e.g., a first sensor, a post-operative sensor) associated with a shoulder joint of the patient, and a wearable sensor device 306 (e.g., a second sensor, a pre-operative sensor), which, in this example, is worn on/about a wrist of the patient 300, but could be worn in any suitable location. The sensors depicted in FIG. 3 are merely illustrative and other sensors in other locations can be used in examples according to this disclosure. In one example, wearable sensor device 306 can be an off-the-shelf consumer wearable device such as, for example, Fitbit, Jawbone, Apple Watch, or other consumer wearable electronic devices, or sensor device 306 can be a custom sensor that is configured to be worn by a patient 300 to collect pre-operative data or post-operative data. Implanted sensors 304 can be employed to collect pre-operative or post-operative data. In some cases, the sensor can be attached to the patient on, proximate or near the site where an orthopedic surgery can be performed. The sensor can be attached via a garment or strap, however it can also be attached to the patient, for example, via a temporary adhesive.

Example Sensor Applications

In some examples, knee sensor technology can include a sensor or sensors to monitor steps, forces, friction, temperature, or the like. Sensors can provide useful data from positions throughout the body. For example, sensors can be embedded in a bone plate spanning a fracture in the user's humerus or femur. As discussed, sensors in bone plates can monitor healing, plate movement, bone screw integrity or movement of the associated limb (e.g., arm or leg). In various examples, the sensor may be attached directly to the bone or be inserted through a bone.

In some examples, the sensor can be used to detect if a screw breaks. Screw failures in plates and nails can occur when the screw breaks in half. The sensor can include a line sensor that extends the length of the screw shaft. If there is a discontinuation in that line, the sensor can report that a screw failure has occurred. In another example, the sensor can include a visual indicator, for example, visible under ultrasound, which can alert a surgeon.

A sensor can be included on a screw head, a sensor in a screw hole, or major circuitry on plate. In some examples, a sensor can: detect a screw back out, measure interaction between a screw and a plate, determine a disconnect of a fastener, such as a screw or nail backout (e.g., pressure on head against bone), monitor a lag screw, perform angulation detection (e.g., within a lag screw), locking mechanism sensing, monitor pH or other analysis such as for infection warning, temperature monitoring, or the like.

In some examples, patient data obtained from sensors described herein can include any suitable data including monitoring screw back-out, detecting when things go wrong (e.g., allowing self-diagnostics for the patient), allowing for day-to-day comparison (e.g., motion/load/deflection, such as on a one-piece plate), monitoring load (e.g., pressure, focus, deflection, etc.), biological factor detection, such as where is the sensor located, what a sensor is detecting, or how the is the data retrieved.

As noted above, in some examples, sensors employed to generate and/or collect post-operative patient and/or implant data can be implanted in the patient (for example, intra or post-operatively). However, in some examples, the sensor can not only generate data, but can also be used to provide remotely controlled stimulus to the surgical site, such as by an electrical, vibrational or ultrasonic stimulus.

Sensor Arrays

Figure 4:
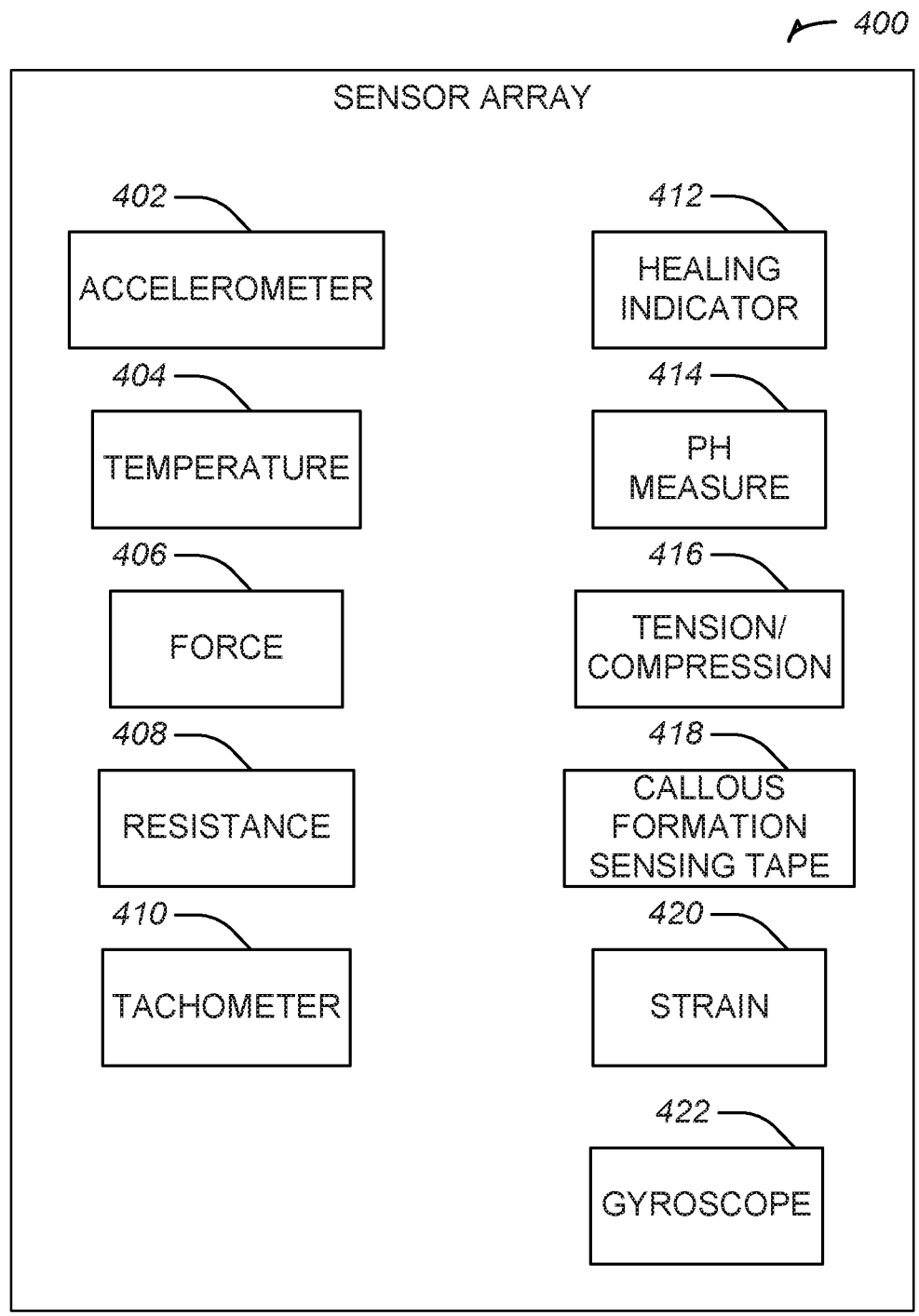
FIG. 4 illustrates an array of sensors for measuring various biological, mechanical, or other patient and/or implant parameters, in accordance with at least one example.

FIG. 4 illustrates an example sensor array 400 including example sensors (e.g., 402-420), which can be employed in examples according to this disclosure. Such a sensor array can be included in a sensor device that is worn by or implanted within a patient before, during, or after an implant surgery.

The example sensor array 400 can include an accelerometer 402, a temperature sensor 404, a force sensor 406, a resistance sensor 408, a tachometer 410, a healing indicator 412, a pH measure sensor 414, a tension or compression sensor 416, callous formation sensing tape 418, a strain sensor 420 (e.g., strain gauge), a gyroscope 422 or the like. More or fewer individual sensors can be included in sensor array 400 or another example sensor array. The sensor array 400 can include active sensors and inactive sensors.

In some examples, a wire tension measurement or a strut measurement, can allow for objective adjustments according to wire or strut tension. Implant adjustments can be made with a verification process via sensors. For example, treatment algorithms can be adjusted based on objective feedback using sensors. Individual measurements can be adjusted, such as by using objective measurements for adjustments.

In some examples, internal bone-based sensors can be used to correlate sensors on an external frame. The combined sensor array can be used to measure bone axis with IM nail sensors, a plate nail, a small sensor (e.g., k-wire), or judge performance based on actual position of bone axis.

Sensor Device System

Figure 5:
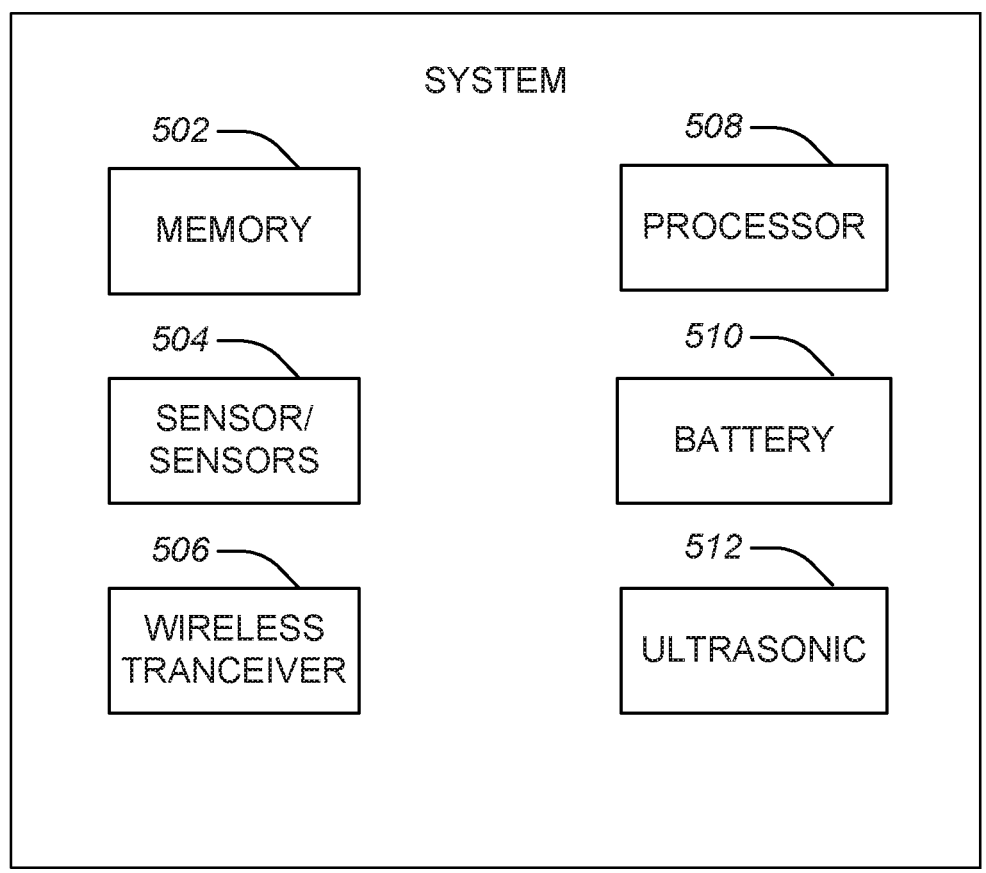
FIG. 5 illustrates a sensor device or system in accordance with at least one example.

FIG. 5 illustrates a sensor device 500 in accordance with some examples. The example sensor device 500 can include any of a sensor, sensors, and/or sensor array 504 (such as sensor array 400 in FIG. 4), memory 502, a wireless transceiver 506, a battery 510 and an ultrasonic sensor 512. A processor 508 can be included in some examples as shown, but as with other components of the device, is not required.

A sensor 504 can be loaded on an implant (e.g., 302 in FIG. 3). The sensor 504 can be used, for example, to monitor steps taken during recovery from a surgery or treatment or to measure parameters related to surgical and/or implant efficacy or performance, including, for example, joint tension. In some examples, the battery 510 can last for 10 years or the battery life of the battery 510 can be dependent on the use of the implant or sensor 504. The wireless transceiver 506 can transmit information, including pre-operative and post-operative sensor data/measurements, using wireless protocols, such as Bluetooth (e.g., Bluetooth Low Energy), 3GPP LTE, WiFi, near field communication (NFC), another healthcare compliant communication protocol, or the like. Sensor device 500 or an associated implant can collect data constantly, or periodically. The collected data can be transmitted, such as routinely, occasionally, or in response to an activation. Activation of a sensor can be based on patient permission, such as post-operation permission when a sensor is included in an implant without pre-operation patient permission to activate. In some examples, access to a sensor in an implant can be an encrypted permission and can rely on an activation code.

A method can include insertion of a sensor, such as into an implant, with an implant, or the like, or externally mounting a sensor. In some examples, a method can include providing a sensor-based patient compliance monitoring system. In some examples, the use of biologics can include using sensor data to provide quantitative data on performance of a patient or implant over-time.

Technology used with a sensor can include a glass scale encoder (e.g., etch marks on implant with a sensor), a photodiode, an ultrasound device (e.g., with an external interrogation device), added marks that can be externally interrogated (e.g., a passive system), or the like.

Example Methods

Figure 6:
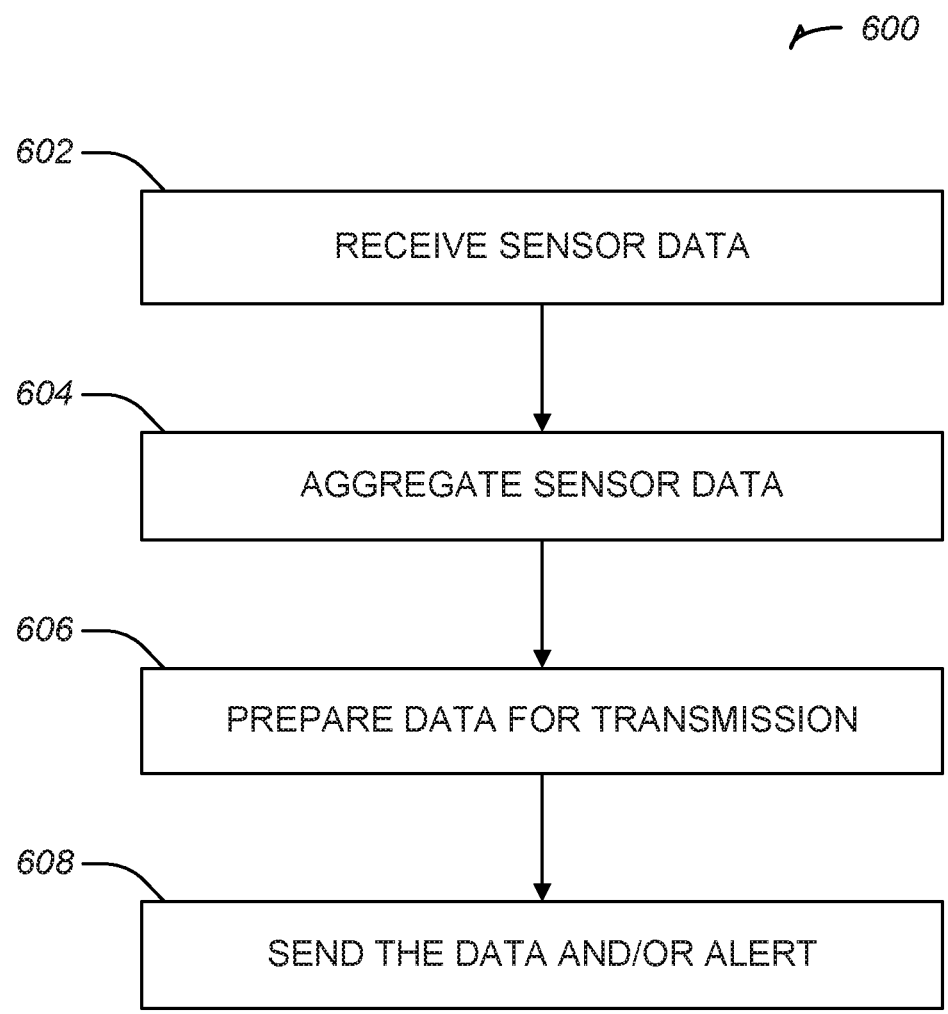
FIG. 6 illustrates a flowchart showing a method for sensor use in accordance with at least one example.

FIG. 6 illustrates a flowchart showing a method for sensor use in accordance with some examples. The method 600 for operating a sensor device may be used with the implantable sensor devices described herein, but aspects of the method 600 may also be used with the wearable devices described herein. As shown in FIG. 6, the method 600 can include operation 602 to receive sensor data. In the present example, the sensor data can include sensor data from a sensor of a bone plate implant. The sensor data can be received at a memory (or via a processor if applicable) of the sensor device.

The method 600 can include operation 604 to aggregate sensor data. Aggregating sensor data can include aggregating the sensor data received in operation 602 with previously received sensor data to be stored in memory. The aggregated data can be aggregated as by a counter type aggregation (e.g., number of occurrences of a type of data point). Aggregating can also include, for example, determining an average, a summary, a mean, a maximum, a minimum, a difference, a sum, or recording measurements in a table or database with or without time stamps. The data can be aggregated either within the sensor device circuitry (such as in a memory or buffer) within the implant, and/or can be done externally via transmission to a remote device (e.g., mobile device or remote device), or to another sensor as part of a wireless mesh network configuration.

The method 600 can include an operation 606 to prepare data for transmission of the data, such as the aggregated sensor data. The data prepared for transmission can be prepared for transmission from the sensor device (e.g., bone implant) to a remote device, such as a mobile device, computer, server, etc. The remote device can be part of a surgical assessment and planning system, which will be described in further detail later in this disclosure. The method 600 can include receiving an indication that the remote device is within a communication range. In some examples, preparing the aggregated sensor data for transmission includes periodically preparing the aggregated sensor data for transmission. In another example, preparing the aggregated sensor data for transmission includes preparing the aggregated sensor data for transmission in response to receiving a wakeup call from the remote device. Preparing the data for transmission may include removing personally identifiable information from the data set upon receiving an indication that the remote device does not have permission to access the personally identifiable information of the patient.

The method 600 includes an operation 608 to send the data. In some examples, the data can be sent in response to receiving the indication that the remote device is within the communication range. In some examples, an alert is sent in place of or in addition to the data. In some examples, data is continuously or periodically sent from sensor devices (nodes) to other nodes in a mesh network; certain nodes may store the data from several sensor devices for subsequent transmission to a remote device. The alert can alert the healthcare provider or patient that the data transgresses a threshold value. The data may also be transmitted when the memory of the sensor device is filled to capacity and data must be successfully transmitted to release the data from memory. The operation 608 to send the data may also include receiving a confirmation at the sensor device that the data was received by the remote device in full or in part. Upon receiving the confirmation, the sensor device may some or all of the data from memory. The operation 608 to send the data may also be triggered when the battery level of the sensor device reaches a critical state.

Various types of data will now be described, including impact force data, strain data and callous formation information. Other types of data may also be sensed, including but not limited to: temperature (e.g., indicator of infection), angle or distance between two sensors e.g., dynamization, a function of fracture healing, or loss of fixation). The use of this data will be described in further detail in the data analysis section that follows.

Example Data: Impact Force

The sensor of method 600 can include a force sensor and the sensor data received from the sensor can include an impact force or number of impacts. Impact force (e.g., load) can help determine the degree of fracture healing or if the device has lost fixation. The method 600 can include further operations such as preparing a durability alert to be transmitted to the remote device when the aggregated sensor data transgresses a durability threshold number of impacts. In another example, a further operation can include preparing an impact alert to be transmitted to the remote device when the impact force transgresses (e.g., exceeds) an impact threshold. In some examples, rather than the sensor device determining if a threshold has been transgressed, the remote device or another part of the surgical planning and assessment system analyzes the aggregated sensor data to determine if an alert should be generated. Other analyses that can be performed outside of the sensor device can include analyzing the data to confirm the alert is correct, or to generate additional alerts. In addition to impact force, thresholds for other aspects, such as strain value and callous formation can be provided, as well as for any other suitable type of sensor data. EXAMPLE DATA: STRAIN VALUE The sensor of method 600 can include operations to obtain data from a strain gauge and the sensor data received from the sensor can include a strain value. Operation 604 to aggregate the sensor data can include determining a maximum strain received from the strain gauge. Strain values will be described in further detail below, for example, in the analysis section.

Example Data: Callous Formation Information

In some examples, the sensor of method 600 can include operations to obtain data from callous formation sensing tape and the sensor data received from the sensor can include callous formation information. Operation 604 to aggregate the sensor data can include determining if the callous formation information indicates that a callous is forming. In response to determining that a callous is forming (e.g., a callous formation value is transgressed), the method 600 can include preparing a callous formation alert to be transmitted to the remote device. Alternatively, the remote device can complete the analysis and generate the alert from the callous formation information.

Analyzing Data

In some examples according to this disclosure, ambulatory sensors can be employed to generate and collect pre-operative patient-specific data, which is employed to prepare a tailored orthopedic surgical plan for the patient. Collecting pre-operative sensor data can be used to predict the performance of an orthopedic implant to be implanted in the patient when such plan is executed, and to compare the predicted performance to the actual performance of the implant post-operatively to quantitatively measure the efficacy of the implant and/or surgery. The pre-operative and intra-operative and/or post-operative sensors can be any of a variety of sensors for measuring relevant biological, mechanical, or other patient and/or implant parameters that can be used to improve the selection, sizing, implantation, etc. of an orthopedic prosthetic implant for the patient. Additionally, ambulatory sensors for pre and post-operative use can be off-the-shelf consumer electronic devices such as, for example, Fitbit, Jawbone, Apple Watch, or other consumer wearable electronic devices that measure various parameters indicative of different aspects of the wearer's physical or mental wellbeing or other characteristics. Alternatively, or in addition to such off-the-shelf wearable devices, sensors can be non-invasively implanted pre-operatively and/or can be included in or implanted with the orthopedic implant intra-operatively and then used to collect post-operative data indicative of parameters like, for example, joint tension in a knee, shoulder, hip or other joint of the patient.

Example Methods: Data Comparison and Analysis

Figure 7:
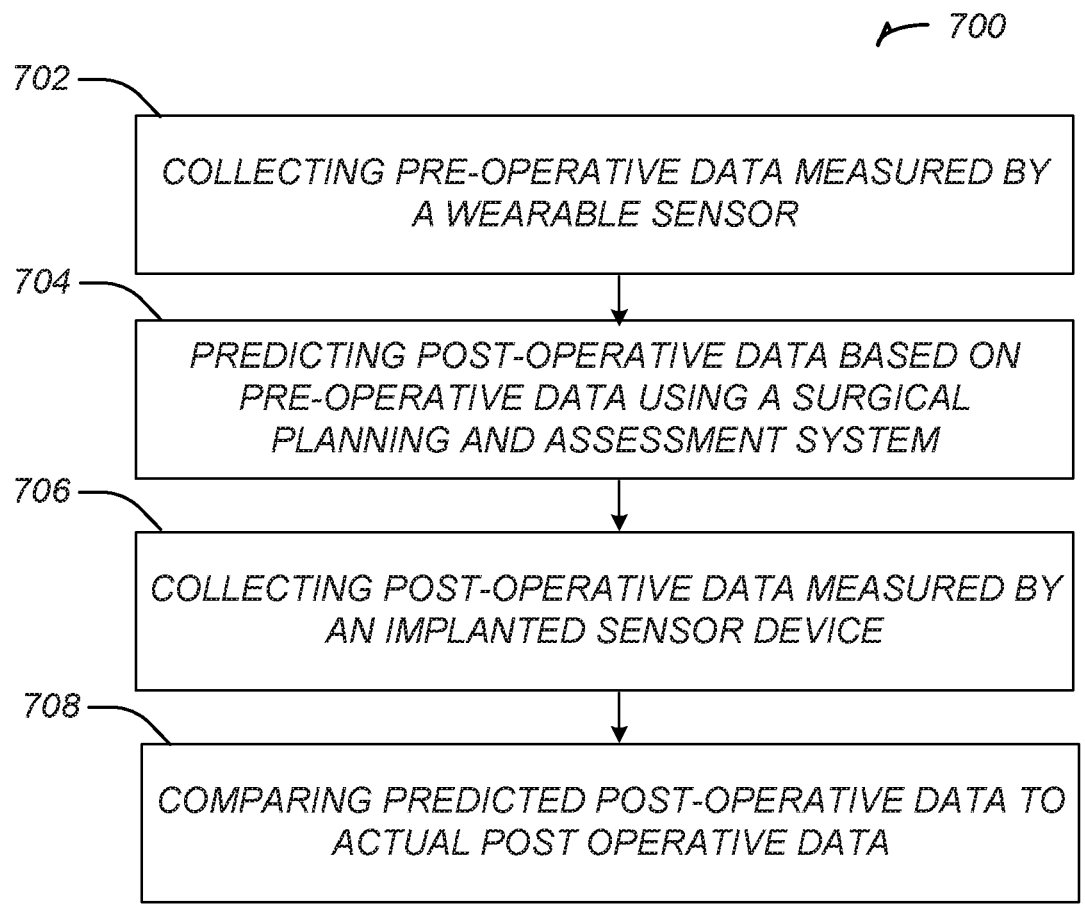
FIG. 7 illustrates a method for collecting and analyzing data in accordance with at least one example.

FIG. 7 is a flowchart depicting illustrative method 700 in accordance with at least one example. Method 700 of FIG. 7 can be used together or separately with any of the implants and sensor devices described herein, or with any other suitable implants and sensor devices.

As shown in FIG. 7, operation 702 can include collecting pre-operative data measured by a pre-operative sensor device (e.g., a wearable sensor device, a first sensor device) worn by or implanted in a patient (e.g., wearable sensor device 306 of FIG. 3). In one example, a healthcare provider can collect data from sensors worn by or implanted in a patient that is a candidate for an orthopedic surgery, prior to an orthopedic surgery on the patient. A variety of sensors and devices including such sensors can be employed to collect pre-operative patient-specific data, examples of which, are described herein. The sensor data is indicative of or can be employed to deduce or calculate mechanical or other properties of the patient's anatomy or other patient-specific characteristics relevant to the planned surgical procedure and/or the potential or predicted performance of the prosthetic device implanted in such procedure. Any of the sensors, wearable, implanted or otherwise, can be used in any of the examples.

Operation 704 can include predicting post-operative data based on the collected pre-operative sensor data. The prediction can be performed using a surgical planning and assessment system 704. The surgical planning and assessment system 704 can be a remote system. In some examples, however, the wearable device itself can generate the predicted post-operative sensor data on a processor that is part of the wearable device.

Factors that can be considered in predicting (e.g., analyzing and translating) the pre-operative sensor data into predicted post-operative sensor data can take into account physical parameters of the patient, such as age, weight, height, gender, race, disease, previous treatments, medications, body mass index (bmi), bone strength, bone density, number of previous fractures, presence of osteoporosis. Other considerations in predicting the post-operative sensor data can include analyzing the pre-operative sensor data in view of the planned surgical procedure (e.g., type of procedure), or differences between the pre-operative sensor and the post-operative sensors (if any). As populations of outcome data become more widely available, additional correlations between pre-operative sensor data and post-operative sensor data can be developed. The systems and methods discuss herein can be modified with updated correlations as they become available to refine the predicted post-operative sensor data for comparison to actual post-operative sensor data in assessing outcomes and/or providing treatment plans. In an example, sensors associated with several different patients can be aggregated, optionally in de-identified form) and stored in a central database. The data stored at the central database can be input into a machine learning or artificial intelligence system to derive updated correlations and additional insights. The central database can include multiple samples of patient data in a variety of patient populations in order to translate the data into results for comparison in the form of loading, angles and temperature, etc.

Operation 706 can include collecting actual post-operative sensor data measured by a second sensor (e.g., post-operative sensor) implanted in or worn by the patient. Collecting the actual post-operative sensor data can also include aggregating the actual post-operative sensor data, such as is shown and described in FIGS. 1-6.

Operation 708 can include comparing the predicted post-operative sensor data to the collected actual post-operative data, which can be aggregated post-operative data as described in method 600 of FIG. 6. Some non-limiting example analyses and comparisons of predicted and actual sensor data will now be described, however any suitable comparison for assessing the outcome of a surgery can be used.

In an example where the sensor data includes strain values, operation 708 can include analyzing/comparing the predicted post-operative sensor data and the aggregated post-operative sensor data to determine if the patient should be more active or less active.

In another example where the sensor data includes strain values, operation 708 can include analyzing/comparing the predicted post-operative sensor data and the aggregated post-operative sensor data to determine if the strain values are within a specified range or if the values transgressed a threshold.

In an example where the sensor data includes a number of impacts or impact force value, operation 708 can include analyzing/comparing the aggregated post-operative sensor data to the predicted post-operative sensor data to determine if the patient should be more active or less active, or to determine if an impact threshold has been transgressed.

In an example where the sensor data includes a number of impacts or impact force value, operation 708 can include analyzing/comparing the aggregated post-operative sensor data and the predicted post-operative sensor data to determine if an impact threshold (e.g., durability threshold) has been transgressed.

In an example where the sensor data includes callous formation information, operation 708 can include analyzing/comparing callous formation information, from the aggregated post-operative sensor data and the predicted post-operative sensor data to determine if the callous formation information is within a specified range or if a callous is forming.

Analyzing/comparing the aggregated post-operative sensor data can include determining a post-operative care plan, or determining an outcome from a treatment being monitored by a sensor, based on a comparison of the aggregated post-operative sensor data to the predicted post-operative sensor data.

In examples described herein, the aggregated post-operative sensor data can be compared to the pre-operative sensor data, without translating the pre-operative sensor data into predicted post-operative sensor data.

Other Data Comparison Methods

In some examples, data or parameters in addition to, or instead of the pre-operative sensor data, can be used in surgical planning and/or post-operative assessments. For example, computerized tomography (CT) or other scans can be employed to model patient anatomy for implant selection and/or one-off custom or semi-custom implant fabrication. In some examples, comparisons can be made to a patient population(s) in order to assess the success of the surgery compared to the patient population(s).

Surgical Planning and Assessment System

An example surgical planning and assessment system can use the collected pre-operative sensor data to predict surgical success, post-operative patient conditions/parameters, and/or post-operative implant performance. For example, the surgical planning and assessment system can compute and store a dataset representing predicted post-operative sensor data (e.g., readings). A second sensor device worn by or implanted within the patient can collect actual post-operative sensor data associated with the patient after the orthopedic surgery is completed. The first and second sensor devices can be the same device or different devices. The predicted surgical success, post-operative patient conditions/parameters, and/or post-operative implant performance can be compared to the actual collected post-operative sensor data. This and other examples methods corresponding to and/or encompassing the foregoing features of examples according to this disclosure and generally shown in the flowcharts of FIG. 6 and FIG. 7 can be implemented in a surgical planning and assessment system. The surgical planning and assessment system can be a remote device or operate in conjunction with the remote device. Any of the sensor data can be input into a surgical planning and assessment system. The surgical planning and assessment system can be a computer-implemented system, and can include a variety of software programs, components, modules, algorithms, hardware components, and combinations thereof. The surgical planning and assessment system can also be configured to communicate over local and wide area networks, including over public and private networks like the Internet (and may include security measures where appropriate or necessary). Communication between the surgical planning and assessment system can be enabled between components or devices, for example, a sensor device worn by or implanted within the patient, can be connected via various wired or wireless transport mediums and according to various proprietary or standards based protocols.

Generally speaking, the surgical planning and assessment system can enable any of a patient, surgeon, other health care provider or manufacturer to plan and manage a surgery, including selection of an optimal implant and, in certain scenarios, different instrumentation options. For example, implants can be a custom made implant made specific to the patient, an implant that is only partially custom-made or a semi-custom made, or a standard off-the shelf implant can be planned for the surgery. Similarly, custom-made, semi-custom made or off-the-shelf instrumentation (e.g. alignment guides, drill guides, cutting guides or other instruments) can be selected and, if applicable, manufactured, as approved by the surgeon, for the surgical procedure.

An assessment is performed comparing the predicted post-operative performance and/or sensor data with the actual post-operative sensor data (e.g., aggregated post-operative sensor data) as described. In one example, the post-operative sensor contains a processor or a number of processors for comparing the predicted and actual results and providing an indication (for example, one or more colored LEDs or other visual indicators) to the healthcare provider and or patient of whether the comparison falls within a predetermined acceptable range and/or whether a delta between predicted and actual results is within a target tolerance. In another example, the collected data and/or surgical plan is read out of the sensor by a healthcare provider and is compared to the actual readings outputted by the (post-operative) sensor. This allows for a healthcare provider without access to the original surgical plan to make an independent assessment of the surgery. Several assessments can be conducted over the lifetime of the patient and/or implant in order to track performance of a surgical implant and to gather data on and/or draw conclusions about the long term prognosis of the patient following surgery. These assessments can be aggregated from several patients in a population, optionally in de-identified form, and can be saved in a central database. The central database can provide inputs to a machine learning or artificial intelligence system that generates correlations used to predict the long term prognosis of the patient following surgery.

In another example, the healthcare provider can have or be granted access to the original surgical plan and/or the collected pre-operative sensor data, and also can have or can be granted access to the post-operative sensor data. In this example, the healthcare provider can have its own computer-implemented system for predicting post-operative sensor data/implant performance and/or comparing the predicted post-operative sensor data to the actual post-operative sensor data.

In an example method of orthopedic surgical assessment after a surgery based on previously described FIGS. 6 and 7, the surgical assessment and planning system works in a complementary manner to the sensor devices. For example, a method performed by a remote device can include activating circuitry operably coupled to a sensor that is implanted in a patient, the circuitry can have a memory including aggregated post-operative sensor data from the sensor. Such a method performed from the perspective of the remote device can include receiving transmission of the aggregated post-operative sensor data from the circuitry, and analyzing the aggregated post-operative sensor data to determine an outcome from a treatment being monitored by the sensor.

Further, in an example where the analyzing step compares the aggregated post-operative sensor data to pre-operative sensor data or predicted post-operative sensor data that is also stored on the memory of the implanted sensor device, the remote device can further include activating the circuitry operably coupled to the sensor and receiving transmission of the aggregated pre-operative sensor data or the predicted post-operative sensor data from the circuitry.

In an example, where the pre-operative sensor data or the predicted post-operative sensor data is stored on a second sensor device, such as a pre-operative wearable sensor device, the method performed by the remote device can include activating a second circuitry operably coupled to a second sensor. The second circuitry can have a second memory including aggregated pre-operative sensor data collected from a second sensor worn by the patient prior to surgery. The remote device can receive transmission of the aggregated pre-operative sensor data from the circuitry, and then analyze the pertinent data to determine an outcome from a treatment monitored by the sensor and the second sensor.

System Packages

All of the implant components, alignment guides, and other reusable or disposable instruments can be included in a package or kit provided to a surgeon for a specific patient, or a patient population. In examples according to this disclosure, the surgical planning and assessment system is also configured to programmatically predict post-operative patient, implant, or other parameters using sensor data collected before the surgery. For example, the system can compute and store a dataset representing predicted post-operative sensor readings.

In one example, the collected pre-operative sensor data and/or surgical plan (including, for example, a dataset predicting post-operative sensor readings) can be downloaded from the surgical planning and assessment system into a small microchip or nonvolatile storage medium, such as a microSD card. This or other example computer-readable storage medium can be inserted into or otherwise communicatively coupled with a sensor device worn by the patient after surgery or implanted in the patient during surgery. Additionally, the computer-implemented storage medium can be inserted into a sensor device implanted into the patient following the orthopedic surgery. Alternatively, the pre-operative sensor data and/or surgical plan can be transferred directly (for example, via short-range wireless communication or via wired communication before the sensor is implanted in or worn by the patient) to computer-readable storage medium included in the sensor device employed to collect post-operative sensor data.

System Architecture

Figure 8:
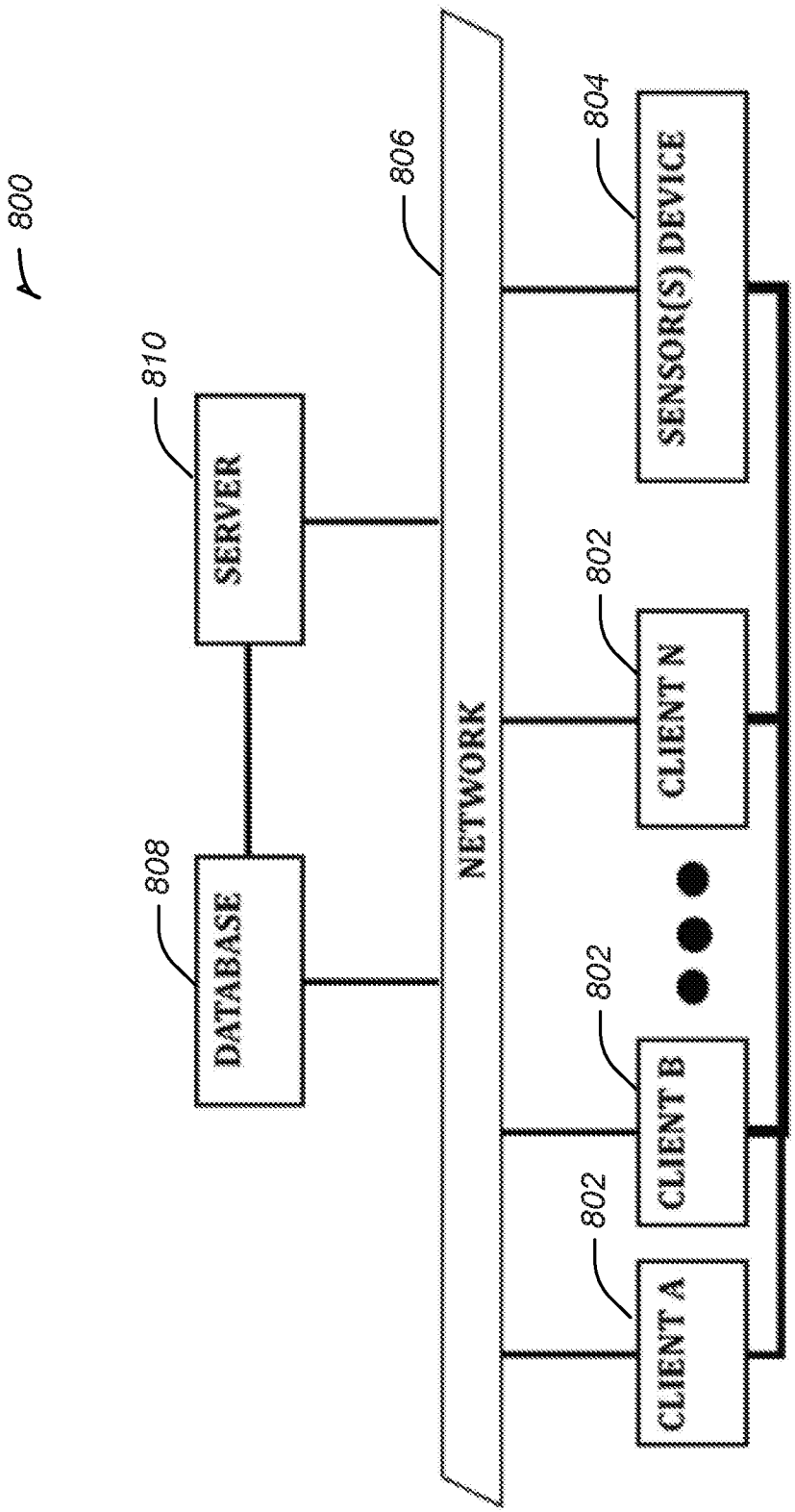
FIG. 8 illustrates an example computer-implemented system in accordance with at least one example FIGS. 9 and 10 generally illustrate example systems including sensor positioning in relation to bones and implants, according to some examples.

FIG. 8 is a block diagram illustrating an example architecture and componentry for a computer-implemented system 800, which can be used in examples according to this disclosure. Example system 800 can include client computing devices 802A, 802B-802N (collectively "clients 802" or individually "client 802"), sensor(s) device(s) 804, network 806, data repository 808 and server 810. Clients 802 can run portions or all of a surgical planning and assessment system. Additionally, clients 802 can be patient, clinician, or healthcare provider electronic devices for monitoring and/or collecting data locally or remotely from sensor(s) device(s) 804 and/or collecting data from or otherwise communicating with server 810 and/or data repository 808 via network 806. Sensor 804 can be any of the pre-operative and/or post-operative sensors employed in examples according to this disclosure, but can also include other suitable sensors. Server 810 can store and execute the surgical planning and assessment system and/or can be associated with external parties, including, for example, implant manufacturers, healthcare providers, etc. Data repository 808 can be associated with and used for multiple data storage functions.

Sensor 804 is communicatively (e.g., operably, electrically) connected to clients 802, data repository 808, and server 810 via network 806. Clients 802, sensor 804, data repository 808, and server 810 are configured to communicate with one another and/or to execute functions alone or in conjunction with one another over network 806. Clients 802 can include any number of different portable electronic mobile devices, including, e.g., cellular phones, personal digital assistants (PDA's), laptop computers, portable gaming devices, portable media players, e-book readers, watches, as well as non-portable devices such as desktop computers. Clients 802 can include one or more input/output devices configured to allow user interaction with one or more programs. In one example, clients 802 run a web browser that accesses/executes and presents a web application for use by the user of the client. In another example, clients 802 execute an application outside of a web browser, e.g. an operating system specific application that accesses/executes and presents a native OS application for use by the user of the client.

Sensor device 804 can be either or both of a pre-operative and a post-operative sensor worn by or implanted within a patient. Sensor device 804 can include a number of different sensors, sensor arrays, including integrated computer-readable storage media and/or processor(s), as described in further detail herein.

Network 806 can include one or more terrestrial and/or satellite networks interconnected to provide a means of communicatively connecting clients 802, sensor(s) device(s) 804, data repository 808 and/or server 810. In one example, network 806 is a private or public local area network (LAN) or Wide Area Network (WANs). Network 806 can include both wired and wireless communications according to one or more standards and/or via one or more transport mediums. In one example, network 806 includes wireless communications according to one of the 802.11 or Bluetooth specification sets, or another standard or proprietary wireless communication protocol. Network 806 can also include communications over a terrestrial cellular network, including, e.g. a GSM (Global System for Mobile Communications), CDMA (Code Division Multiple Access), EDGE (Enhanced Data for Global Evolution) network. Data transmitted over network 806, e.g., from sensor 804 to clients 802 and/or to data repository 808 and server 810 can be formatted in accordance with a variety of different communications protocols. For example, all or a portion of network 806 can be a packet-based, Internet Protocol (IP) network that communicates data in Transmission Control Protocol/Internet Protocol (TCP/IP) packets, over, e.g., Category 5, Ethernet cables.

Data repository 808 can include, e.g., a standard or proprietary electronic database or other data storage and retrieval mechanism. In one example, data repository 808 includes one or more databases, such as relational databases, multi-dimensional databases, hierarchical databases, object-oriented databases, or one or more other types of databases. Data repository 808 can be implemented in software, hardware, and combinations of both. In one example, data repository 808 include proprietary database software stored on one of a variety of storage mediums on a data storage server connected to network 806 and configured to store data such as measured/collected pre-operative sensor data, predicted post-operative data or other information, and/or measured/collected post-operative sensor data, including aggregated post-operative sensor data. Storage media included in or employed in cooperation with data repository 808 can include, e.g., any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Data repository can be employed to store and retrieve pre and/or post-operative sensor data. Additionally, data repository 808 can store and retrieve data or other information from analytics executed on sensor data and/or a surgical plan, as well as data and other information related to patient population modeling.

Server 810 can be any of several different types of network and/or computing devices. Examples of server 810 include a data processing appliance, web server, specialized media server, personal computer operating in a peer-to-peer fashion, or another type of networked device. Additionally, although example system 800 of FIG. 8 includes one server 810, other examples include a number of collocated or distributed servers configured to process data, surgical plans, etc. individually or in cooperation with one another. Although data repository 808 and server 810 are illustrated as separate components in example system 800 of FIG. 8, in other examples, the components are combined or each can be distributed amongst more than one device.

Server 810 can host and execute portions or all of the surgical planning and assessment system. Additionally, server 810 or another server or other device connected thereto can include a data analytics system for processing and analyzing sensor data (pre and post-operative), surgical plans, and other information relevant to surgical planning and post-operative assessment.

Data Users

In some examples, the sensor data collected from the patient pre-operatively, the surgical plan, and the sensor data collected from the patient post-operatively can be input into a data analytics or other computer-implemented system for modeling population health, developing predictive analytics, and/or assessing patient outcomes. In one example, the data fed into the data analytics system is provided to or shared with a payor. The data can be collected through a wired connection from the sensor to a central control unit, computer server, or other electronic device located at the healthcare provider's facility. This central control unit can establish a wide-area or other connection to a server controlled by the healthcare provider or medical device manufacturer that maintains the data analytics system. Alternatively, data from the sensor can be transmitted wirelessly through Wi-Fi, ZigBee, Bluetooth, or other wireless communications to the central control unit for re-transmission via wide-area network to the server. In one example, the central control unit performs intermediate data processing steps such as data anonymization or encryption prior to transmission to the data analytics system.

Example Sensor Relationship to Bones and Implants

Figure 9:
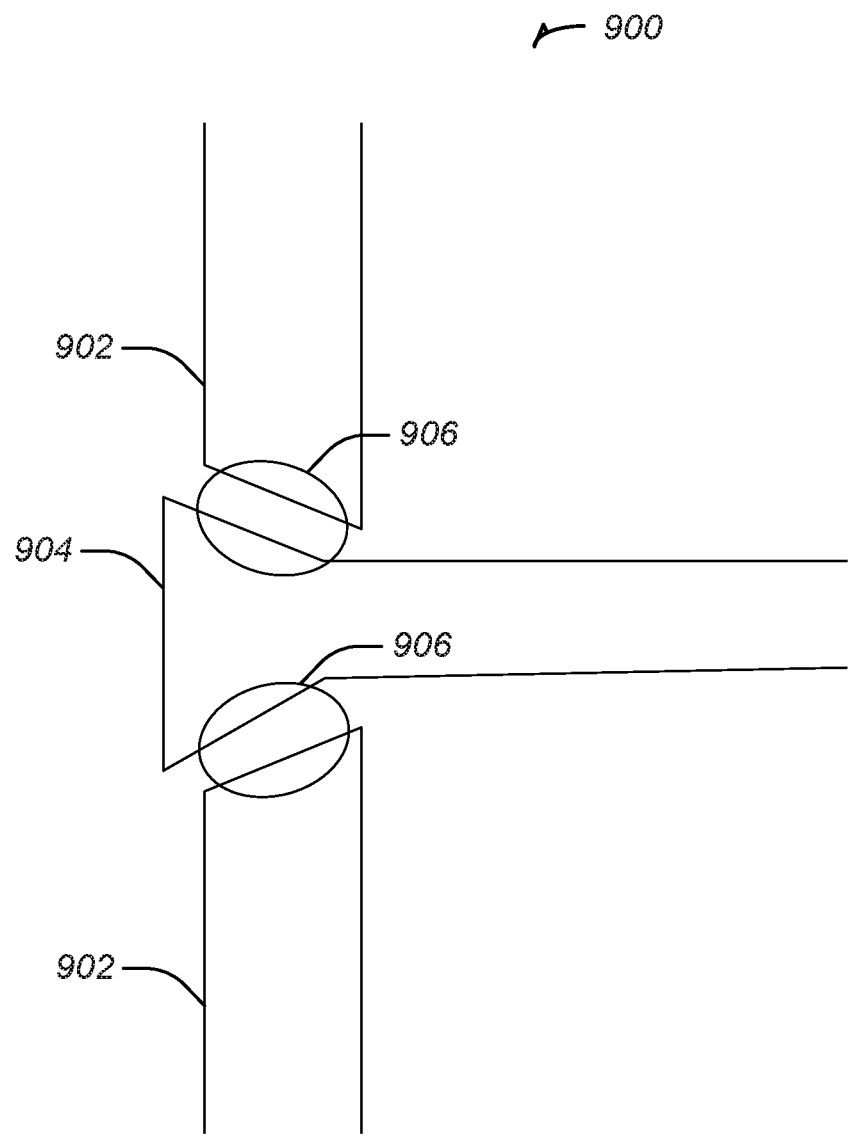
Figure 10:
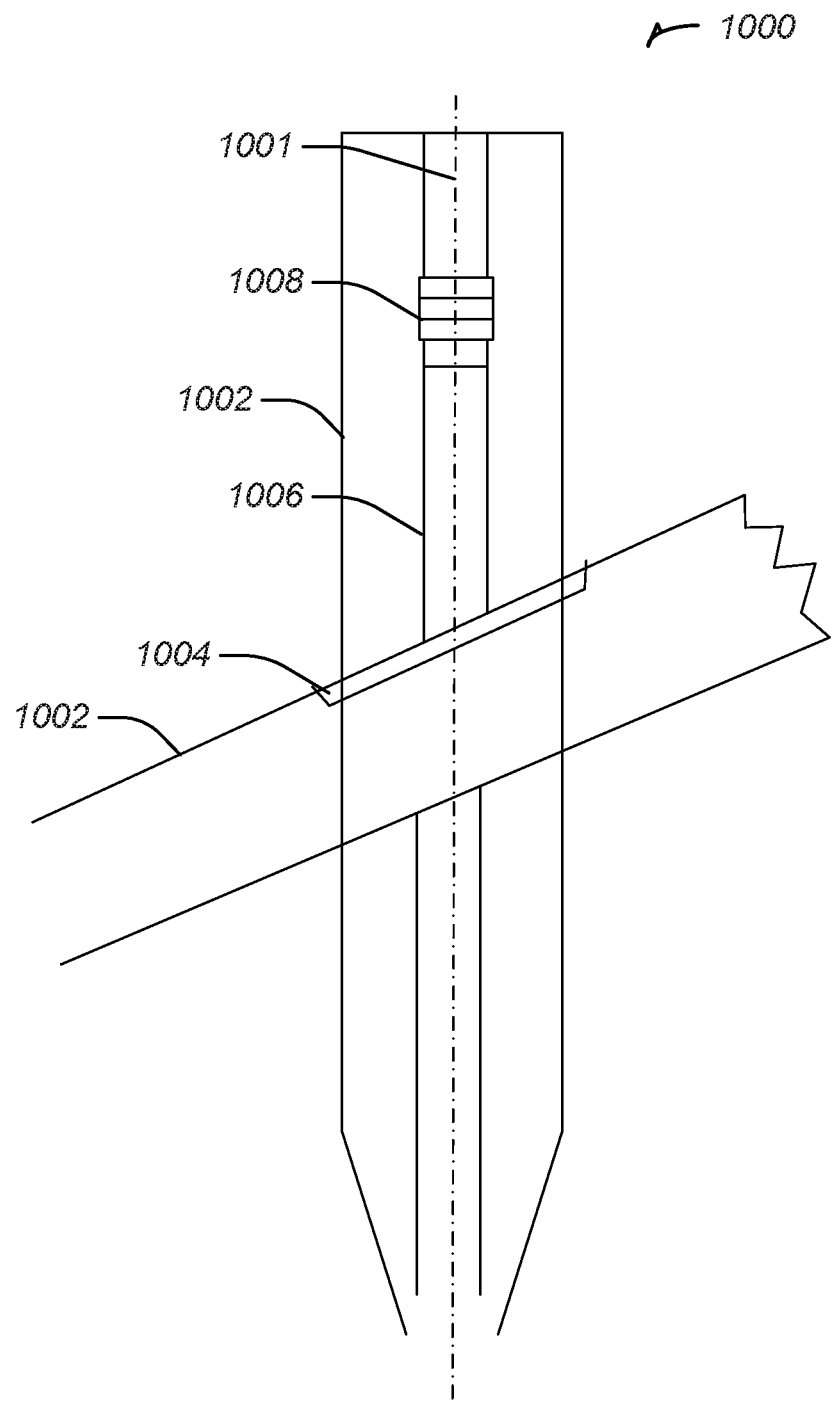

FIGS. 9 and 10 provide a general illustration of example systems including sensor positioning in relation to bones and bone implants that can be used with the sensors and methods described herein. FIG. 9 illustrates a system 900 including bone 902 and an implant 904, with sensor locations 906 to monitor wear on the bone 902 or the implant 904. FIG. 10 illustrates a system 1000 including bone 1002, and a cross-section 1004 of the bone to show an implant 1006. The implant 1006 can include a first sensor 1008 or a second sensor along the shaft (e.g. or a specified axis 1001) of the implant 1006.

Example Machine

Figure 11:
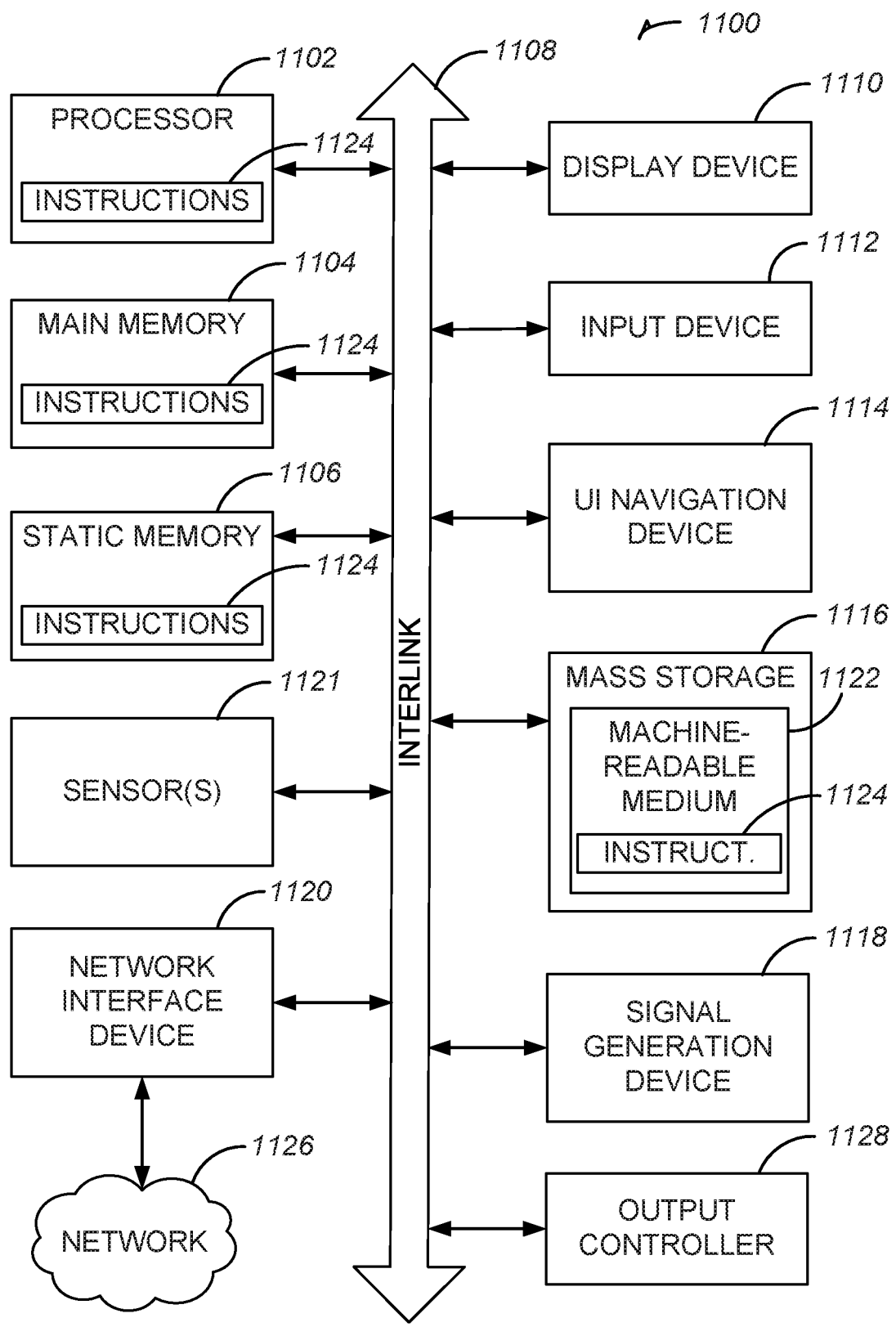
FIG. 11 generally illustrates an example block diagram of a machine upon which any one or more of the methods discussed herein can perform in accordance with at least one example.

FIG. 11 is a general illustration of an example block diagram of a machine 1100 upon which any one or more of the methods (e.g., techniques) discussed herein can perform in accordance with some examples. In alternative examples, the machine 1100 can operate as a standalone device or can be connected (e.g., networked) to other machines. In a networked deployment, the machine 1100 can operate in the capacity of a server machine, a client machine, or both in server-client network environments. In some examples, the machine 1100 can act as a peer machine in peer-to-peer (P2P) (or other distributed) network environment. The machine 1100 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, can include, or can operate on, logic or a number of components, modules, or mechanisms. Modules are tangible entities hardware) capable of performing specified operations when operating. A module includes hardware. In some examples, the hardware can be specifically configured to carry out a specific operation (e.g., hardwired). In some examples, the hardware can include configurable execution units (e.g., transistors, circuits, etc) and a computer readable medium containing instructions, where the instructions configure the execution units to carry out a specific operation when in operation. The configuring can occur under the direction of the executions units or a loading mechanism. Accordingly, the execution units are communicatively coupled to the computer readable medium when the device is operating. In this example, the execution units can be a member of more than one module. For example, under operation, the execution units can be configured by a first set of instructions to implement a first module at one point in time and reconfigured by a second set of instructions to implement a second module.

Machine (e.g., computer system) 1100 can include a hardware processor 1102 (e.g., a central processing unit (CPU), a graphics processing unit (GPU), a hardware processor core, or any combination thereof), a main memory 1104 and a static memory 1106, some or all of which can communicate with each other via an interlink (e.g., bus) 1108. The machine 1100 can further include a display unit 1110, an alphanumeric input device 1112 (e.g., a keyboard), and a user interface (UI) navigation device 1114 (e.g., a mouse). In some examples, the display unit 1110, alphanumeric input device 1112 and UI navigation device 1114 can be a touch screen display. The machine 1100 can additionally include a storage device (e.g., drive unit) 1116, a signal generation device 1118 (e.g., a speaker), a network interface device 1120, and one or more sensors 1121, such as a global positioning system ((SPS) sensor, compass, accelerometer, or other sensor. The machine 1100 can include an output controller 1128, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Storage Device Machine Readable Medium

The storage device 1116 can include a machine readable medium 112.2 that is non-transitory on which is stored one or more sets of data structures or instructions 1124 (e.g., software) embodying or utilized by any one or more of the techniques or functions described herein. The instructions 1124 can also reside, completely or at least partially, within the main memory 1104, within static memory 1106, or within the hardware processor 1102 during execution thereof by the machine 1100. In some examples, one or any combination of the hardware processor 1102, the main memory 1104, the static memory 1106, or the storage device 1116 can constitute machine readable media.

While the machine readable medium 1122 is illustrated as a single medium, the term "machine readable medium" can include a single medium or multiple media (e.g., a centralized or distributed database, or associated caches and servers) configured to store the one or more instructions 1124.

The term "machine readable medium" can include any medium that is capable of storing, encoding, or carrying instructions for execution by the machine 1100 and that cause the machine 1100 to perform any one or more of the techniques of the present disclosure, or that is capable of storing, encoding or carrying data structures used by or associated with such instructions. Non-limiting machine readable medium examples can include solid-state memories, and optical and magnetic media. Specific examples of machine readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1124 can further be transmitted or received over a communications network 1126 using a transmission medium via the network interface device 1120 utilizing any one of a number of transfer protocols (e.g., frame relay, internet protocol (IP), transmission control protocol (TCP), user datagram protocol (UDP), hypertext transfer protocol (LTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In some examples, the network interface device 1120 can include one or more physical jacks (e.g., Ethernet, coaxial, or phone jacks) or one or more antennas to connect to the communications network 1126. In some examples, the network interface device 1120 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1100, and includes digital or analog communications signals or other intangible medium to facilitate communication of such software.

The foregoing systems and devices, etc. are merely illustrative of the components, interconnections, communications, functions, etc. that can be employed in carrying out examples in accordance with this disclosure. Different types and combinations of sensor or other portable electronics devices, computers including clients and servers, implants, and other systems and devices can be employed in examples according to this disclosure.

VARIOUS NOTES & EXAMPLES

Each of these non-limiting examples can stand on its own, or can be combined in various permutations or combinations with one or more of the other examples.

Example 1 describes a system including a wearable sensor device for pre-operative use by a patient that is a candidate for an orthopedic surgery. The wearable sensor device configured to generate pre-operative sensor data associated with the patient prior to the orthopedic surgery on the patient. In addition to the wearable sensor device, the system can also include an implantable sensor device configured to be implanted into the patient during or after the orthopedic surgery. The implantable sensor device can be configured to generate and aggregate post-operative sensor data associated with the patient after the orthopedic surgery. The system can also include a surgical planning and assessment system, the system can include at least one computer-readable storage device, wherein the at least one computer-readable storage device is configured to store data and executable instructions; and at least one processor configured to access information stored on the at least one computer-readable storage device and to perform operations. The operations can include retrieving the pre-operative sensor data generated by the wearable sensor device; predicting post-operative sensor data based at least in part on the pre-operative sensor data; retrieve the aggregated post-operative sensor data generated by the implantable sensor device; and analyze the aggregated post-operative sensor data to determine an outcome from a treatment monitored by the implantable sensor device by comparing the predicted post-operative sensor data and the aggregated post-operative sensor data.

In Example 2, the subject matter of Example 1 optionally includes wherein to analyze the post-operative sensor data includes at least one of: compare strain values, from the aggregated post-operative sensor data and the predicted post-operative sensor data, to determine if the patient should be more active or less active; compare a number of impacts or impact force value, from the aggregated post-operative sensor data and the predicted post-operative sensor data, to determine if the patient should be more active or less active; and compare callous formation information, from the aggregated post-operative sensor data and the predicted post-operative sensor data, to determine if a callous is forming.

In Example 3, the subject matter of any one or more of Examples 1-2 optionally include wherein to analyze the aggregated post-operative sensor data includes at least one of: compare strain values, from the aggregated post-operative sensor data and the predicted post-operative sensor data to determine if the strain values are within a specified range; compare callous formation information, from the aggregated post-operative sensor data and the predicted post-operative sensor data, to determine if the callous formation information is within a specified range; and compare a number of impacts or impact force value, from the aggregated post-operative sensor data and the predicted post-operative sensor data, to determine if an impact threshold has been transgressed.

In Example 4, the subject matter of any one or more of Examples 1-3 optionally include wherein analyzing the aggregated post-operative sensor data includes determining a post-operative care plan based on a comparison of the aggregated post-operative sensor data to the predicted post-operative sensor data.

In Example 5, the subject matter of any one or more of Examples 1-4 optionally include wherein predicting the post-operative sensor data includes analyzing the pre-operative sensor data in view of a planned surgical procedure.

In Example 6, the subject matter of any one or more of Examples 1-5 optionally include wherein predicting the post-operative sensor data includes analyzing the pre-operative sensor data in view of physical parameters of the patient.

Example 7 describes a method of orthopedic surgical assessment after a surgery, the method can include activating circuitry operably coupled to a sensor that is implanted in a patient, the circuitry having a memory including aggregated post-operative sensor data from the sensor; receiving transmission of the aggregated post-operative sensor data from the circuitry; and analyzing the aggregated post-operative sensor data to determine an outcome from a treatment being monitored by the sensor.

In Example 8, the subject matter of Example 7 optionally includes wherein analyzing the aggregated post-operative sensor data includes analyzing data gathered from the sensor coupled to a bone or a bone implant.

In Example 9, the subject matter of any one or more of Examples 7-8 optionally include accessing pre-operative sensor data collected from a wearable sensor device worn by the patient prior to the surgery, and wherein analyzing the aggregated post-operative sensor data includes comparing the aggregated post-operative sensor data to pre-operative sensor data.

In Example 10, the subject matter of any one or more of Examples 7-9 optionally include wherein the pre-operative sensor data is stored in the memory, the method further including: activating the circuitry operably coupled to the sensor, the circuitry having the memory including the pre-operative sensor data; and receiving transmission of the pre-operative sensor data from the circuitry, wherein analyzing the aggregated post-operative sensor data includes comparing the aggregated post-operative sensor data to the pre-operative sensor data.

In Example 11, the subject matter of any one or more of Examples 7-10 optionally include wherein predicted post-operative sensor data is stored in the memory, the method further including: activating the circuitry, the circuitry having the memory including the predicted post-operative sensor data; and receiving transmission of the predicted post-operative sensor data from the circuitry, wherein analyzing the aggregated post-operative sensor data includes comparing the aggregated post-operative sensor data to the predicted post-operative sensor data.

In Example 12, the subject matter of any one or more of Examples 7-11 optionally include wherein analyzing the post-operative sensor data includes at least one of: analyzing a strain values from the aggregated post-operative sensor data to determine if the patient should be more active or less active; analyzing a strain value from the aggregated post-operative sensor data to determine if the strain value is within a specified range; analyzing callous formation information from the aggregated post-operative sensor data to determine whether a bone is healing; analyzing callous formation information from the aggregated post-operative sensor data to determine if a callous is forming; analyzing a number of impacts or impact force value from the aggregated post-operative sensor data to determine if the patient should be more active or less active; and analyzing a number of impacts or impact force value from the aggregated post-operative sensor data to determine if an impact threshold has been transgressed.

In Example 13, the subject matter of any one or more of Examples 7-12 optionally include activating a second circuitry operably coupled to a second sensor, the second circuitry having a second memory including pre-operative sensor data collected from a second sensor worn by the patient prior to surgery; and receiving transmission of the pre-operative sensor data from the second circuitry, wherein analyzing the aggregated post-operative sensor data includes comparing the aggregated post-operative sensor data to the pre-operative sensor data to determine an outcome from a treatment monitored by the sensor and the second sensor.

In Example 14, the subject matter of any one or more of Examples 7-13 optionally include wherein the aggregated post-operative sensor data comprises impact force data, and the method further comprises receiving transmission of a durability alert from the circuitry if the impact force transgresses a durability threshold number of impacts.

In Example 15, the subject matter of any one or more of Examples 7-14 optionally include wherein the aggregated post-operative sensor data comprises impact force data, and wherein analyzing the aggregated post-operative sensor data includes determining if the impact force transgresses a durability threshold number of impacts and generating a durability alert if the durability threshold number of impacts is transgressed.

In Example 16, the subject matter of any one or more of Examples 7-15 optionally include wherein the aggregated post-operative sensor data comprises strain value data, and the method further comprises receiving transmission of a strain alert from the circuitry if the strain value data transgresses a threshold strain value.

In Example 17, the subject matter of any one or more of Examples 7-16 optionally include wherein the aggregated post-operative sensor data comprises strain value data, and wherein analyzing the aggregated post-operative sensor data includes determining if the strain value data transgresses a threshold strain value and generating a strain alert if the threshold strain value is transgressed.

In Example 18, the subject matter of any one or more of Examples 7-17 optionally include wherein the aggregated post-operative sensor data comprises callous formation information to indicate if a callous is forming, and the method further comprises receiving transmission of a callous formation alert from the circuitry if the callous formation information transgresses a threshold callous formation value.

In Example 19, the subject matter of any one or more of Examples 7-18 optionally include wherein the aggregated post-operative sensor data comprises callous formation information to indicate if a callous is forming, and wherein analyzing the aggregated post-operative sensor data includes determining if the callous formation information transgresses a threshold callous formation value and generating a callous formation alert if the threshold callous formation value is transgressed.

In Example 20, the subject matter of any one or more of Examples 7-19 optionally include wherein analyzing the aggregated post-operative sensor data includes comparing the aggregated post-operative sensor data to predicted post-operative sensor data, wherein the predicted post-operative sensor data is based on pre-operative sensor data collected from a wearable sensor device worn by the patient prior to surgery.

In Example 21, the subject matter of any one or more of Examples 7-20 optionally include wherein analyzing the aggregated post-operative sensor data includes determining a post-operative care plan based on a comparison of the aggregated post-operative sensor data to the predicted post-operative sensor data.

In Example 22, the subject matter of any one or more of Examples 7-21 optionally include wherein analyzing the aggregated post-operative sensor data includes determining if a post-operative care plan should be adjusted based on a comparison of the aggregated post-operative sensor data to at least one of the predicted post-operative sensor data, the pre-operative sensor data and a pre-operative plan.

In Example 23, the subject matter of any one or more of Examples 7-22 optionally include activating a second circuitry operably coupled to a second sensor, the second circuitry having a second memory including pre-operative sensor data collected from the second sensor worn by the patient prior to surgery; receiving transmission of the pre-operative sensor data from the second circuitry; and analyzing the pre-operative sensor data, and generating corresponding predicted post-operative sensor data, wherein analyzing the aggregated post-operative sensor data includes comparing the aggregated post-operative sensor data to the predicted post-operative sensor data to determine an outcome from a treatment monitored by the sensor and the second sensor.

In Example 24, the subject matter of Example 23 optionally includes wherein the pre-operative sensor data is collected from a wearable sensor device; and wherein the analyzing the pre-operative sensor data includes translating the pre-operative sensor data into predicted post-operative sensor data based on a set of known differences between the wearable sensor device and the sensor implanted in the patient.

Example 25 describes a machine readable medium including instructions that, when executed by a machine, cause the machine to perform operations including: receiving, at a bone implant coupled to a bone of a patient, sensor data from a sensor in the bone implant; aggregating the sensor data with previously received sensor data to be stored in memory; preparing aggregated post-operative sensor data for transmission to a remote device; receiving an indication that the remote device is within a communication range; and sending the aggregated post-operative sensor data to the remote device.

In Example 26, the subject matter of Example 25 optionally includes wherein preparing the aggregated post-operative sensor data for transmission includes periodically aggregating data received from the sensor into the aggregated post-operative sensor data for transmission.

In Example 27, the subject matter of any one or more of Examples 25-26 optionally include wherein preparing the aggregated post-operative sensor data for transmission includes preparing the aggregated post-operative sensor data for transmission in response to receiving a wakeup call from the remote device.

In Example 28, the subject matter of any one or more of Examples 25-27 optionally include wherein the sensor is a force sensor and the sensor data received from the sensor includes an impact force.

In Example 29, the subject matter of Example 28 optionally includes wherein the instructions include further instructions to perform operations including: detecting, based on received impact force data, occurrence of an impact to the bone of the patient; recording, within the aggregated post-operative sensor data, the impact to the bone; determining whether the aggregated post-operative sensor data transgresses a durability threshold number of impacts; and when the durability threshold number of impacts is transgressed, preparing a durability alert to be transmitted to the remote device.

In Example 30, the subject matter of any one or more of Examples 28-29 optionally include wherein the instructions include further instructions to perform operations including determining whether the impact force transgresses an impact threshold, and preparing an impact alert to be transmitted to the remote device.

In Example 31, the subject matter of any one or more of Examples 25-30 optionally, include wherein the sensor is a strain gauge and the sensor data received from the sensor includes a strain value.

In Example 32, the subject matter of Example 31 optionally includes wherein aggregating the sensor data includes determining a maximum strain received from the strain gauge.

In Example 33, the subject matter of any one or more of Examples 25-32 optionally include wherein the sensor includes callous formation sensing tape and the sensor data received from the sensor includes callous formation information.

In Example 34, the subject matter of Example 33 optionally includes wherein aggregating the sensor data includes determining if the callous formation information indicates that a callous is forming.

In Example 35, the subject matter of Example 34 optionally includes wherein in response to determining that the callous formation information indicates that the callous is forming, preparing a callous formation alert to be transmitted to the remote device.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, in some examples, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." in this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

Various aspects of the disclosure have been described. These and other aspects are within the scope of the following claims.

What is claimed is:

1. A system comprising:
a bone implant configured to be coupled to a bone of a patient in an orthopedic procedure;
one or more sensors coupled to the bone implant, the one or more sensors configured to generate sensor data, wherein the one or more sensors includes a deflection sensor, the deflection sensor including a flexible sensor configured to stretch across a fracture of the bone; and
circuitry including a memory, the circuitry coupled to the bone implant and operably coupled to the one or more sensors to receive, aggregate and store the sensor data, including deflection data, and to prepare the stored aggregated sensor data to be transmitted to a remote device.

2. The system of claim 1, wherein the one or more sensors is a sensor array, and wherein to aggregate the sensor data includes aggregating sensor data received from the sensor array, wherein the sensor data includes one or more of: force data, the deflection data, pressure data, strain data, accelerometer data, temperature data, resistance data, pH data, gyroscope data, angle data, distance data, position data, proximity data, friction data, speed data, and callous formation information.

3. The system of claim 1, wherein the aggregated sensor data includes at least one of: a number of occurrences of an event, an average, a mean, a maximum, a minimum, a difference, and a sum.

4. The system of claim 1, wherein the one or more sensors includes at least one of: an accelerometer, a temperature sensor, a force sensor, a resistance sensor, a tachometer, a pH sensor, a sensing tape, a strain gauge, a gyroscope, an angle sensor, a distance sensor, a proximity sensor, and a sensing coil.

5. The system of claim 1, wherein to prepare the aggregated sensor data to be transmitted to a remote device includes removing personally identifiable information.

6. The system of claim 1, wherein the circuitry is configured to periodically aggregate the sensor data.

7. The system of claim 1, wherein the circuitry is configured to determine that the aggregated sensor data exceeds a threshold value and to transmit an alert to the remote device.

8. The system of claim 1, further comprising: the remote device, wherein the remote device is configured to analyze the aggregated sensor data to determine an outcome from a treatment by comparing the aggregated sensor data to predicted post-operative sensor data.

9. The system of claim 8, wherein comparing the aggregated sensor data to the predicted post-operative sensor data comprises calculating a difference between the aggregated sensor data and the predicted post-operative sensor data and determining if the difference is within a target tolerance.

10. The system of claim 1, wherein the bone implant is a knee implant.

11. The system of claim 1, wherein the deflection sensor is configured to produce the deflection data based on deflection data due to callous formation in the bone.

12. The system of claim 1, wherein the deflection sensor is configured to produce the deflection data based on measured remodeling of the bone.

13. A non-transitory machine readable medium including instructions that, when executed by a machine, cause the machine to perform operations comprising:
receiving, at a bone implant coupled to a bone of a patient in an orthopedic procedure,
sensor data from one or more sensors coupled to the bone implant or the bone of the patient, the one or more sensors including an impact force sensor and the sensor data including impact force data;
aggregating the sensor data with previously received sensor data to be stored in memory, wherein aggregating the sensor data includes determining a number of impacts based on the impact data;
preparing the aggregated sensor data for transmission to a remote device;
receiving an indication that the remote device is within a communication range; and
sending the aggregated sensor data to the remote device.

14. The non-transitory machine readable medium of claim 13, wherein receiving sensor data from the one or more sensors coupled to the bone implant includes receiving the sensor data from a sensor array, and wherein aggregating the sensor data includes aggregating the sensor data received from the sensor array.

15. The non-transitory machine readable medium of claim 13, wherein the sensor data includes one or more of: the impact force data, deflection data, pressure data, strain data, accelerometer data, temperature data, resistance data, pH data; gyroscope data, angle data, distance data, position data proximity data, friction data, speed data, and callous formation information.

16. The non-transitory machine readable medium of claim 13, wherein aggregating the sensor data includes determining at least one of: a number of occurrences of an event, an average, a mean, a maximum, a minimum, a difference, and a sum.

17. The non-transitory machine readable medium of claim 13, wherein preparing the aggregated sensor data comprises removing personally identifiable information from the sensor data.

18. The non-transitory machine readable medium of claim 13, wherein aggregating the sensor data includes periodically aggregating the sensor data.

19. The non-transitory machine readable medium of claim 13, further comprising transmitting an alert to the remote device when it is determined that the aggregated sensor data exceeds a threshold value.

20. The non-transitory machine readable medium of claim 13, further comprising transmitting a durability alert to the remote device when the number of impacts transgresses a durability threshold number of impacts.

* * * * *